United States Patent
Yamamoto et al.

(10) Patent No.: US 7,462,683 B2
(45) Date of Patent: Dec. 9, 2008

(54) DIHALIDE, POLYMER COMPOUND AND METHOD FOR PRODUCING THE SAME

(75) Inventors: Takakazu Yamamoto, Kanagawa (JP); Hiroki Fukumoto, Kanagawa (JP); Takahiro Asao, Kanagawa (JP)

(73) Assignee: Tokyo Institute of Technology, Tokyo (JP)

( * ) Notice: Subject to any disclaimer, the term of this patent is extended or adjusted under 35 U.S.C. 154(b) by 131 days.

(21) Appl. No.: 10/598,107

(22) PCT Filed: Feb. 15, 2005

(86) PCT No.: PCT/JP2005/002272

§ 371 (c)(1),
(2), (4) Date: Aug. 17, 2006

(87) PCT Pub. No.: WO2005/078002

PCT Pub. Date: Aug. 25, 2005

(65) Prior Publication Data

US 2007/0185306 A1    Aug. 9, 2007

(30) Foreign Application Priority Data

Feb. 18, 2004    (JP) .............................. 2004-041996

(51) Int. Cl.
C08G 65/34 (2006.01)
C08G 61/00 (2006.01)
C07F 7/04 (2006.01)
C07F 7/18 (2006.01)
C07C 43/20 (2006.01)
C07C 43/225 (2006.01)

(52) U.S. Cl. .................. 528/425; 528/40; 556/465; 556/482; 568/660; 568/661

(58) Field of Classification Search .................. None
See application file for complete search history.

(56) References Cited

FOREIGN PATENT DOCUMENTS

EP    1 074 600 A    2/2001
JP    409077854 A  * 3/1997
JP    10-273523    10/1998
WO    WO 2005/014689    2/2005
WO    WO 2005/014689 A    2/2005
WO    WO 2005/030827    4/2005
WO    WO 2005/030828    4/2005

OTHER PUBLICATIONS

English abstract of JP409077854A, published Mar. 1997.*
Frank Uckert: "Neue I sliche Poly(para-phenylen)-Derivate mit uberbruckten Biphenyl-U"; Dissertation zur Erlangung des Grades Doktor der Naturwissenschaften im Fachbereich Chemie und Pharmazie der Johannes Gutenberg-Universitaet in Mainz, 1998, pp. 1-210, XP00230981 * p. 63-p. 96 * p. 166-p. 176 *.
Yamamoto T et al: "Synthesis of soluble poly(9,10-dihydrophenanthrene-2,7-diyl)s. A new class of luminescent poly(p-phenylene)s with ethylene type bridges"; Polymer, Elsevier Science Publishers B.V., GB, vol. 45, No. 24, Nov. 2004, pp. 8085-8089, XP004619237; ISSN: 0032-3861 * abstract *.
Supplementary European Search Report 05710222.0-1214 PCT/JP2005002272, May 10, 2007.

* cited by examiner

*Primary Examiner*—Rosalynd Keys
(74) *Attorney, Agent, or Firm*—Greenberg Traurig, LLP

(57) ABSTRACT

It is an object of the invention to provide a novel π-conjugated polymer compound capable of expecting an application as a functional material having a solubility, a heat resistance, an electrochemical activity and a fluorescence, and a method for producing the same.

A dihalide is represented by the following formula:

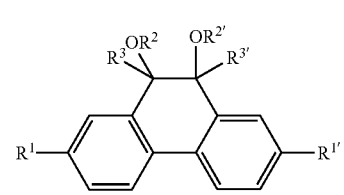

[Formula 1]

(wherein $R^1$ represents a halogen, $R^2$ represents an alkyl group or a silyl group having a substituent, and $R^3$ represents a hydrogen or an alkyl group).

14 Claims, 4 Drawing Sheets

DIHALIDE, POLYMER COMPOUND AND METHOD FOR PRODUCING THE SAME

This application is a national stage filing under 35 U.S.C. 371 of International Application PCT/JP2005/002272, filed on Feb. 15, 2005, which claims the benefit of Japanese application No: 2004-041996, filed on Feb. 18, 2004. The entire teachings of the referenced Application is incorporated herein by reference. International Application PCT/JP2005/002272 was published under PCT Article 21(2) in English.

TECHNICAL FIELD

This invention relates to a dihalide, a polymer compound and a method for producing the same, and more particularly to a dihalide having a specific structure in its main chain and a polymer compound, and a method for producing the polymer compound obtained by using the dihalide as a starting material.

BACKGROUND ART

Recently, an aromatic polymer compound is noticed as a material having heat resistance, electrochemical activity and fluorescence, and the application and development, for example, as a fluorescence material are advanced. For example, polyaniline, polythiophene and the like are expected to have a function as an active material for a cell through the application of its electrochemical redox reaction (A. G. MacDiarmid et al., PCT Int. Appl. 82-US299) (Yamamoto, Matsunaga, "Polymer Battery", Kyoritsu Publication (1990)).

Also, it is expected that a polyparaphenylene-based polymer has a high heat resistance, and poly(9,10-dihydrophenanthrene-2,7-diyl) is synthesized, in which benzene rings in a polyparaphenylene are bonded with an ethylene group (polym. Bull., vol. 30, p 285 (1993)).

Non-patent document 1: A. G. MacDiarmid et al. PCT Int. Appl. 82-US299, Yamamoto, Matsunaga, "Polymer Battery", Kyoritsu Publication (1990)

Non-patent document 2: polym. Bull., vol. 30, p 285 (1993)

DISCLOSURE OF THE INVENTION

Problems to be Solved by the Invention

However, the conventionally developed poly(9,10-dihydrophenanthrene-2,7-diyl) is insoluble in a solvent, so that it has restrictions such as limitation of moldability and so on. Therefore, it is demanded to develop polyparaphenylene-based polymers having an electrochemical activity, a heat resistance, a fluorescence and a high solubility.

It is, therefore, an object of the invention to provide a novel poly(9,10-dihydrophenanthrene-2,7-diyl) introduced with a suitable substituent for solubilization and capable of expecting the application as a functional material, and a method for producing the same.

Means for Solving Problems

The inventors have made various studies about a dihalide and dehalogenation of the dihalide in order to achieve the above objects and found a polymer compound according to the invention and a method for producing the same.

That is, the dihalide according to the invention is represented by the following formula:

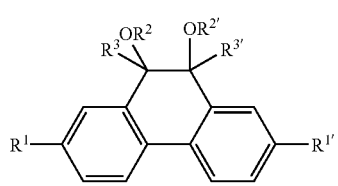

[Formula 1]

(wherein $R^1$ and $R^{1'}$ represent a halogen, $R^2$ and $R^{2'}$ represent an alkyl group or a silyl group having a substituent, and $R^3$ and $R^{3'}$ represent hydrogen or an alkyl group, provided that $R^1$ and $R^{1'}$, $R^2$ and $R^{2'}$, and $R^3$ and $R^{3'}$ may be different or the same).

In a preferable embodiment of the dihalide according to the invention, the silyl group having the substituent is at least one selected from the group consisting of $Si(CH_3)_3$, $Si(n\text{-}C_4H_9)_3$, $Si(t\text{-}C_4H_9)_3$, $Si(CH_3)_2(C_6H_5)$ and $Si(CH_3)_2(n\text{-}C_{18}H_{37})$.

Moreover, in another preferable embodiment of the dihalide according to the invention. the alkyl group is an alkyl group having a carbon number of 1-20.

Also, the polymer compound according to the invention is characterized by having a structure represented by the following formula in its main chain:

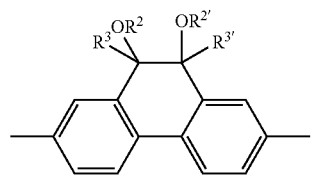

[Formula 2]

(wherein $R^2$ and $R^{2'}$ represent an alkyl group or a silyl group having a substituent, and $R^3$ and $R^{3'}$ represent hydrogen or an alkyl group).

The polymer compound according to the invention is preferable to be represented by the following formula:

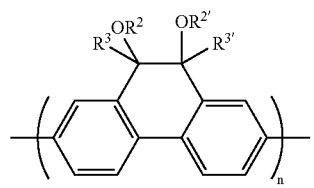

[Formula 3]

(wherein $R^2$ and $R^{2'}$ represent an alkyl group or a silyl group having a substituent, $R^3$ and $R^{3'}$ represent hydrogen or an alkyl group, and n represents a polymerization degree and is 5-1000.)

Also, the polymer compound according to the invention is preferable to be composed of a copolymer comprising a structure represented by the formula described in claim 4 and another structure.

In a preferable embodiment of the polymer compound according to the invention, the copolymer is at least one selected from the group consisting of the following formulae:

[Formula 4]

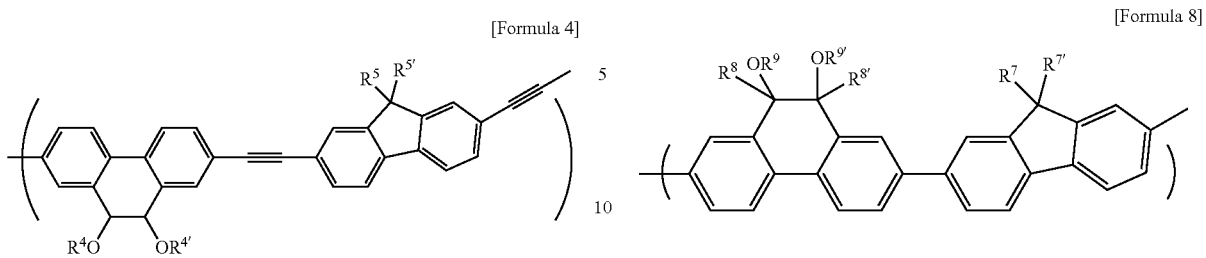

(wherein $R^4$, $R^{4'}$, $R^5$ and $R^{5'}$ represent an alkyl group, provided that $R^4$ and $R^{4'}$, and $R^5$ and $R^{5'}$ may be different or the same),

[Formula 5]

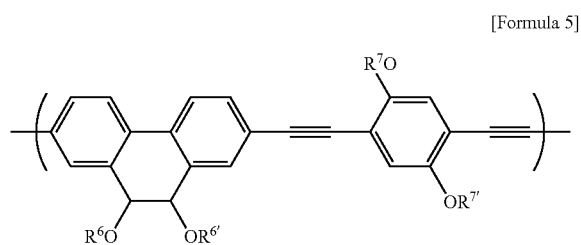

(wherein $R^6$ and $R^{6'}$ represent a silyl group having a substituent, and $R^7$ and $R^{7'}$ represent an alkyl group, provided that $R^6$ and $R^{6'}$, and $R^7$ and $R^{7'}$ may be different or the same),

[Formula 6]

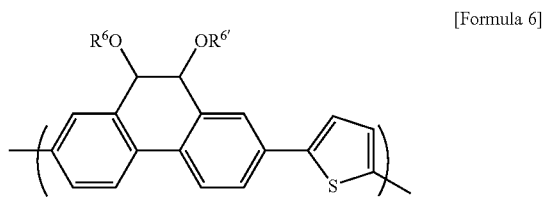

(wherein $R^6$ and $R^{6'}$ represent a silyl group having a substituent, provided that $R^6$ and $R^{6'}$ ray be different or the same),

[Formula 7]

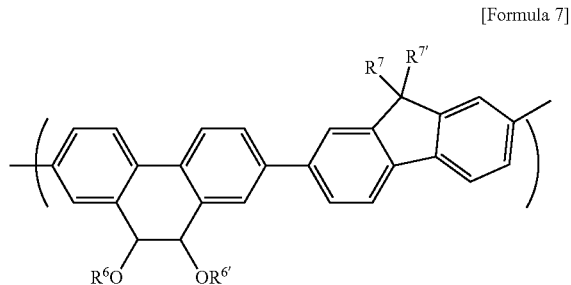

(wherein $R^6$ and $R^{6'}$ represent a silyl group having a substituent, and $R^7$ and $R^{7'}$ represent an alkyl group, provided that $R^6$ and $R^{6'}$, and $R^7$ and $R^{7'}$ may be different or the same), and

[Formula 8]

(wherein $R^7$, $R^{7'}$, $R^8$, $R^{8'}$, $R^9$ and $R^{9'}$ represent an alkyl group, provided that $R^7$ and $R^{7'}$, $R^8$ and $R^{8'}$, and $R^9$ and $R^{9'}$ may be different or the same).

The method for producing the polymer compound according to the invention is characterized by dehalogenation-polymerizing the dihalide to obtain the polymer compound according to the invention.

In a preferable embodiment of the method for producing the polymer compound according to the invention, the dehalogenation-polymerization is carried out in the presence of a palladium or nickel compound.

Effects of the Invention

The dihalide according to the invention develops an advantageous effect capable of providing a useful conjugated polymer compound as an electrochemically and engineeringly functional material.

The polymer compound and the method for producing the same according to the invention develop an advantageous effect capable of simply providing a novel polyparaphenylene-based polymer having moldability owing its solubility, a heat resistance, a fluorescence and an electrochemical activity. Particularly, a thin film can be obtained by selecting an alkyl group or a silyl group having a substituent and using a method comprising steps of dissolving in a solvent and then casting.

BEST MODE FOR CARRYING OUT THE INVENTION

Figure 1:
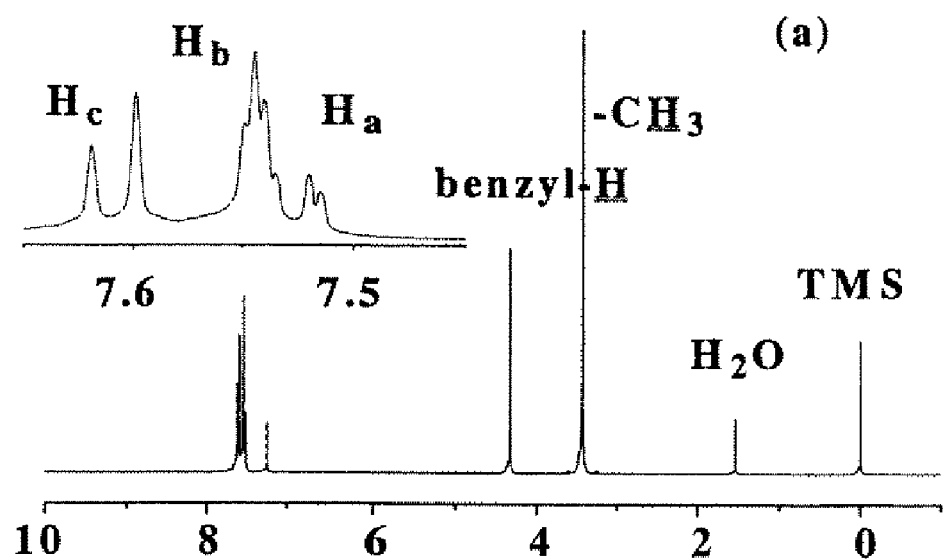
FIG. 1 is a NMR spectrum of a compound 6 in Formula 25.

That is, the dihalide according to the invention is represented by the following formula.

[Formula 9]

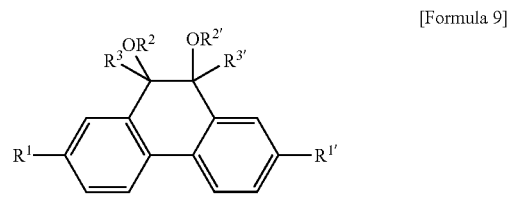

In the above formula, $R^1$ and $R^{1'}$ represent a halogen selected from Cl, Br, I and so on, and are preferably Br in view of synthesis easiness and high reactivity. The halogens selected as $R^1$ and $R^{1'}$ may be different from each other, but are preferably the same in view of the synthesis easiness. $R^2$ and $R^{2'}$ represent an alkyl group or a silyl group having a substituent. $R^3$ and $R^{3'}$ represent a hydrogen or an alkyl group. From a viewpoint of improving solubility of the resulting polymer, $R^2$, $R^{2'}$, $R^3$ and $R^{3'}$ are preferable to have a certain molecular chain length (for example, $R^3$ and $R^{3'}$ are an alkyl group having a carbon number of 1-20), but are not limited thereto. $R^2$ and $R^{2'}$, and $R^3$ and $R^{3'}$ may be different or the same.

Also, the polymer compound according to the invention has a structure represented by the following formula in its main chain.

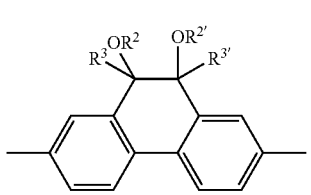

[Formula 10]

In the formula, $R^2$ and $R^{2'}$ represent an alkyl group or a silyl group having a substituent (hereinafter may be referred to as a substituted silyl group), and $R^3$ and $R^{3'}$ represent a hydrogen or an alkyl group. $R^2$ and $R^{2'}$, and $R^3$ and $R^{3'}$ may be different or the same. That is, the polymer compound of the invention is not particularly limited about its structure, as far as it has the structure represented by [Formula 10] in its main chain, and may have another constitutional unit (for example, ones derived from pyridine, phenanthrene, thiophene and so on) within a range not obstructing the heat resistance, fluorescence and electrochemical activity in addition to the repeating constitutional unit represented by [Formula 10], but is particularly preferable to be the polymer compound composed of the structure represented by [Formula 10]. In this case, it may be a homopolymer having the same repeating constitutional unit of [Formula 10], or a copolymer having a combination of different repeating constitutional units of [Formula 10], but is preferable to be the homopolymer in view of synthesis easiness and characteristics.

The molecular weight of the polymer compound according to the invention is not particularly limited in accordance with its applications, but is preferably not less than 1000, and more preferably 3000-100000 as a weight average molecular weight. The polymer has advantages that the molding is easy and the strength of the molded product is improved as it has such a molecular weight.

Also, the polymer compound according to the invention is represented by the following formula.

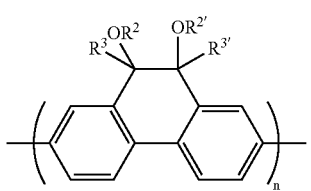

[Formula 11]

In the formula, $R^2$ and $R^{2'}$ represent an alkyl group or a substituted silyl group, and $R^3$ and $R^{3'}$ represent a hydrogen or an alkyl group. $R^2$ and $R^{2'}$, and $R^3$ and $R^{3'}$ may be different or the same. Moreover, n represents a polymerization degree and is 5-1000. Since the polymer compound of the invention has solubility in an organic solvent such as chloroform or the like, it is easy to apply a solution of the polymer compound onto a substrate such as a glass or the like. From a viewpoint of the improvement of the solubility, $R^2$ and $R^{2'}$ are desirable to be silyl group having an approximately C1-C20 alkyl group and $R^3$ and $R^{3'}$ are desirable to be an approximately C1-C20 alkyl group, but they are not particularly limited to them.

Moreover, in a preferable embodiment of the polymer compound according to the invention, it is composed of a copolymer comprising a structure represented by the formula described in claim 3 and another structure. Such a copolymer is not particularly limited, but for example, includes at least one selected from the group consisting of the following formulae:

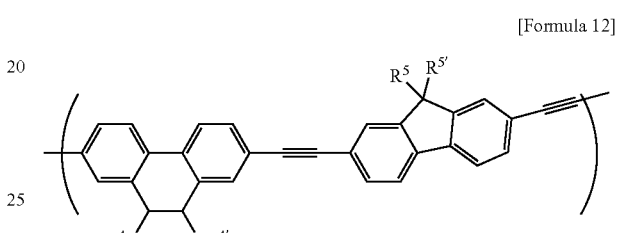

[Formula 12]

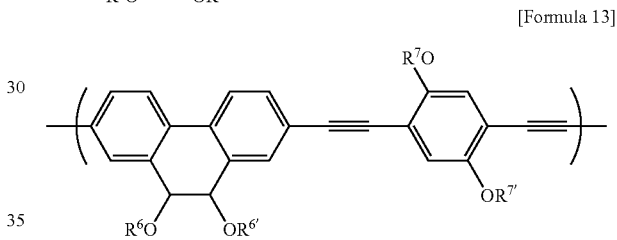

[Formula 13]

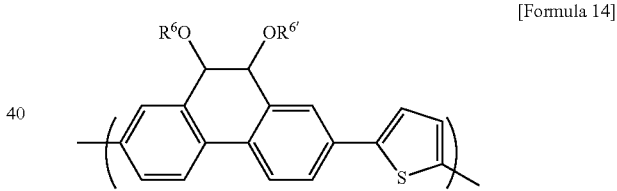

[Formula 14]

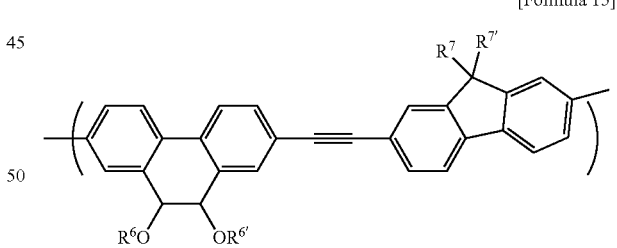

[Formula 15]

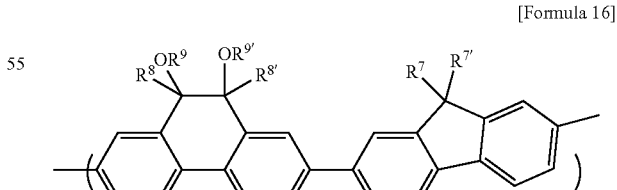

[Formula 16]

(wherein $R^4$, $R^{4'}$, $R^5$ and $R^{5'}$ represent an alkyl group, $R^6$ and $R^{6'}$ represent a silyl group having a substituent, $R^7$, $R^{7'}$, $R^8$, $R^{8'}$, $R^9$ and $R^{9'}$ represent an alkyl group, and $R^4$ and $R^{4'}$, $R^5$ and $R^{5'}$, $R^6$ and $R^{6'}$, $R^7$ and $R^{7'}$, $R^8$ and $R^{8'}$, and $R^9$ and $R^{9'}$ may be different or the same).

The method for producing the polymer compound according to the invention will be described below. In the method for producing the polymer compound according to the invention, the polymer compound of the invention can be obtained by dehalogenation-polymerizing the above-described dihalide. In a preferable embodiment, the dehalogenation-polymerization is carried out in the presence of a palladium or nickel compound in view of the high reactivity.

As a metal or a metal compound used for the homopolymer of the invention are mentioned various ones. At first, as the metal is desirable a reducing metal or a metal causing a C—C coupling reaction of an organic halide, and mention may be made of metals of Group 1 such as Li, Na, K and so on; metals of Group 2 such as Mg, Ca and so on; transition metals such as Ti, V, Cr, Fe, Co, Ni, Cu and so on; metals of Group 12 such as Zn and so on; metals of Group 13 such as Al, Ga and so on; and metals of Group 14 such as Sn and so on. As the metal can be used catalysts comprising other metals or metal compounds, if necessary (there is described an example in which a nickel compound is used as a catalyst in a similar polymerization using Mg in the formula (1) of "Polymer", vol. 46, p 68 (1997)). Also, the metal compound is not particularly limited, but is preferable to be a reducing metal compound or one causing a C—C coupling reaction of an organic halide, and includes, for example, a zero-valent nickel compound, a zero-valent palladium compound and the like. When these zero-valent metal compounds are used, they may be used in themselves or they may be produced by adding a divalent nickel compound, a divalent palladium compound or the like and using a reducing agent such as Zn, hydrazine or the like in a reaction system. As a single polymerization system using the zero-valent nickel compound and accompanying a formation of C—C bond is mentioned the polymerization system described in JP-A-H06-42428. Also, in the coupling reaction using a palladium catalyst can be used a coupling reaction of an acetylene $R^{10}C{\equiv}C$— with an organic halide $R^{15}X$, or a coupling reaction of an organic tin or boron compound (for example, $R^{12}SnR^{13}{}_3$ or $R^{14}Sn$—$B(OR^{15})_3$) with a $R^{11}X$.

Among them, the palladium or nickel compound is preferable in view of high reactivity. In case of obtaining the homopolymer, it is preferable to use a zero-valent nickel complex (for example, bis(1,5-cyclooctadiene) nickel:Ni$(cod)_2$).

Such a reaction may be performed by using an organic solvent such as dimethylformamide (DMF) or the like at a temperature of about 20-120° C.

The thus obtained polymer compound can be identified by an elemental analysis, an infrared absorption spectrum (IR) or the like. Also, the molecular weight is determined by a gel permeation chromatography (GPC) method.

The polymer compound according to the invention is soluble and is expected as a polymer material having a heat resistance, an electrochemical activity and a fluorescence.

Also, the polymer compound according to the invention can be used as an electrochromic material because it shows an electrochemical reduction accompanied with a change of color. Furthermore, it can be used as an active material for a cell utilizing an oxidation-reduction function. A concrete application method and embodiment thereof are according to well-known ones.

EXAMPLES

The following examples are given in illustration of the invention and are not intended as limitations thereof. Moreover, needless to say, they can be properly modified without departing from the scope of the invention.

Example 1

Synthesis of Dihalide

A reaction scheme of the dihalide according to the invention is shown below,

[Formula 17]

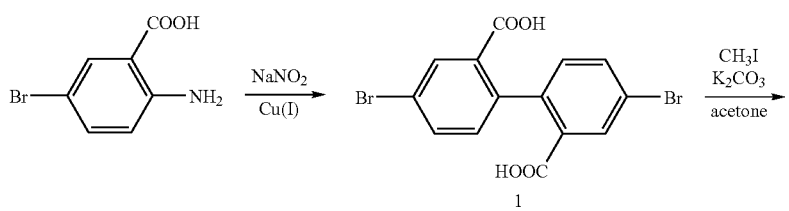

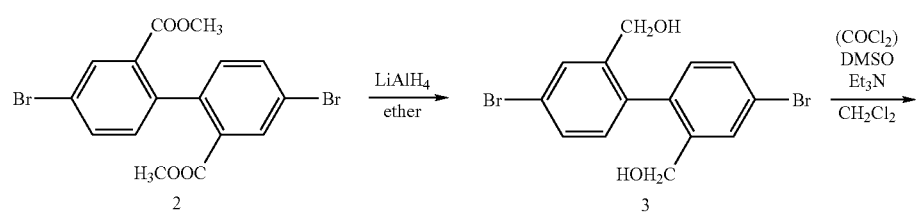

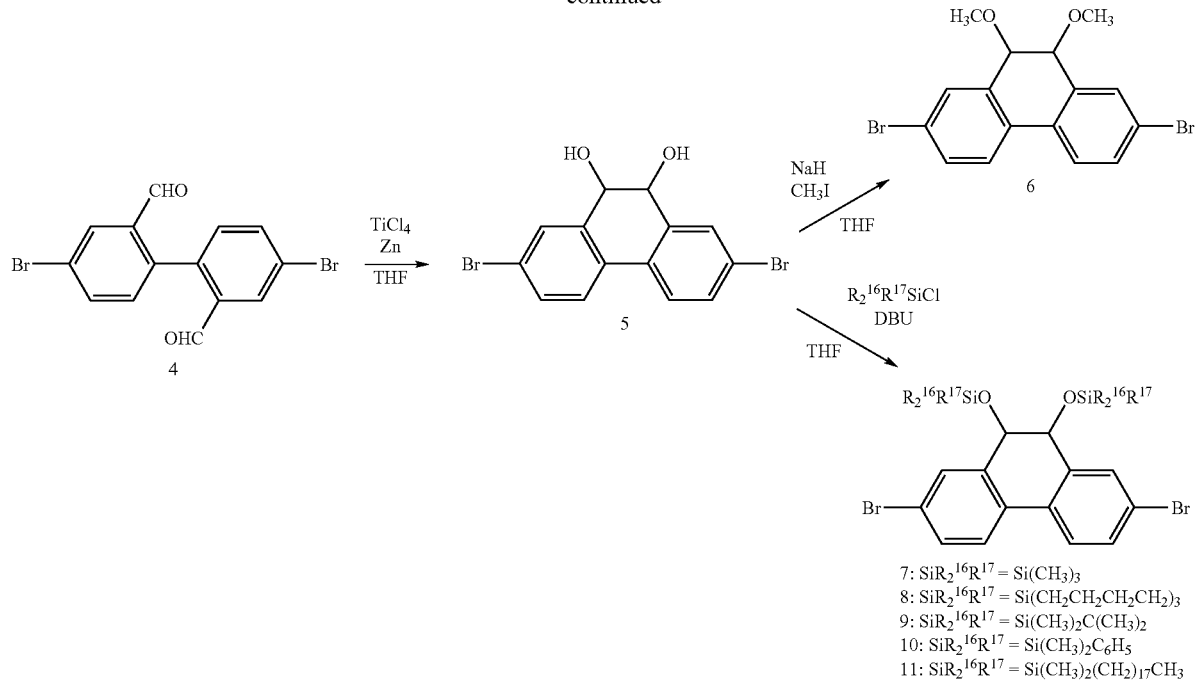

7: SiR$_2^{16}$R$^{17}$ = Si(CH$_3$)$_3$
8: SiR$_2^{16}$R$^{17}$ = Si(CH$_2$CH$_2$CH$_2$CH$_2$)$_3$
9: SiR$_2^{16}$R$^{17}$ = Si(CH$_3$)$_2$C(CH$_3$)$_2$
10: SiR$_2^{16}$R$^{17}$ = Si(CH$_3$)$_2$C$_6$H$_5$
11: SiR$_2^{16}$R$^{17}$ = Si(CH$_3$)$_2$(CH$_2$)$_{17}$CH$_3$ (A) Synthesis of 4,4'-dibromo-2,2'-dicarboxy-1,1'-biphenyl (1)

To 2-amino-5-bromobenzoic acid (5.47 g, 25.3 mmol) are added H$_2$O (20 mL) and hydrochloric acid (9 mL), which is cooled to 0° C. and further added with sodium nitrite (2.10 g, 30.4 mmol) and stirred for one hour. Then, copper(II) sulfate pentahydrate (12.6 g, 50.5 mmol) is dissolved in H$_2$O (45 mL) and added with 30% ammonia solution (22 mL), to which is added a solution of hydroxyammonium chloride (3.76 g, 55.7 mmol) in 6N-sodium hydroxide (9 mL) at 0° C. and stirred. To the resulting solution is added a diazotized solution dropwise from below a liquid level of the copper solution over 30 minutes. The resulting solution is turned to a room temperature, stirred for 2 hours and heated for one hour.

The solution is made to be acidic with a hydrochloric acid, suction-filtered and dried. 4,4'-Dibromo-2,2'-dicarboxy-1,1'-biphenyl (4.5 g, 11.3 mmol, 90%) is obtained as a yellow powder by purifying through a column chromatography (hexane:ethyl acetate=1:1). The thus obtained powder is recrystallized with chloroform to obtain a white plate crystal.

(Characteristics)

$^1$H NMR (CD$_3$OD, 400 MHz) δ (ppm)=8.10 (d, J=1.95 Hz, 2H, H$_a$) 7.69 (dd, J=1.95, 8.30 Hz, 2H, H$_b$) 7.10 (d, J=8.30 Hz, 2H, H$_c$) IR (KBr), 3099, 1708, 1585, 1417, 1298, 1281, 1248, 1096, 1003, 826 (cm$^{-1}$), J. Am. Chem. Soc., 1992, 114, 6227.

In the above characteristics, H$_a$, H$_b$ and H$_c$ belong to hydrogens bonded with a benzene ring (hereinafter they do likewise in the following examples).

(B) Synthesis of 4,4'-dibromo-2,2'-bis(methoxycarbonyl)-1,1'-biphenyl (2)

To 4,4'-dibromo-2,2'-dicarboxy-1,1'-biphenyl (0.18 g, 0.46 mmol) are added potassium carbonate (0.84 g, 6.00 mmol), acetone (25 mL) and iodomethane (170 μL, 2.73 mmol) in a nitrogen atmosphere and refluxed for 2 hours.

The resulting mass is extracted with a chloroform, dried with an anhydrous magnesium sulfate and concentrated. By purifying through the column chromatography (hexane:chroloform=1:1) is obtained 4,4'-dibromo-2,2'-bis(methoxycarbonyl)-1,1'-biphenyl (0.18 g, 0.42 mmol, 91%) as a yellow powder. The thus obtained powder is recrystallized with a mixed solvent of chloroform and hexane to obtain a white plate crystal.

(Characteristics)

$^1$H NMR (CDCl$_3$, 400 MHz) δ (ppm), 8.16 (d, J=1.95 Hz, 2H, H$_a$) 7.66 (44, J=1.95, 8.30 Hz, 2H, H$_b$) 7.04 (d, J=8.30 Hz, 2H, H$_c$) 3.66 (s, 6H, —CH$_3$) IR (KBr), 1730, 1716, 1434, 1294, 1278, 1244, 1148, 1095, 971, 832 (cm$^{-1}$)

(C) Synthesis of 4,4'-dibromo-2,2'-bis(hydroxymethyl)-1,1'-biphenyl (3)

4,4'-Dibromo-2,2'-bis(methoxycarbonyl)-1,1'-biphenyl (3.24 g, 7.56 mmol) is dissolved in a dry ether (42 mL) and stirred at 0° C. under a nitrogen atmosphere. Further, the solution is added with lithium aluminum hydride (0.64 g, 16.9 mmol) and stirred for 6 hours.

The resulting mass is extracted with an ethyl acetate, dried with an anhydrous magnesium sulfate and concentrated. By purifying through the column chromatography (hexane:ethyl acetate=1:1) is obtained 4,4'-dibromo-2,2'-bis(hydroxymethyl)-1,1'-biphenyl (2.60 g, 6.98 mmol, 92%) as a white powder. The thus obtained powder is recrystallized with a mixed solvent of chloroform and hexane to obtain a white plate crystal.

(Characteristics)

$^1$H NMR (DMSO, 400 MHz) δ (ppm)=7.69 (d, J=1.71 Hz, 2H, H$_a$) 7.47 (dd, J=2.20, 8.05 Hz, 2H, H$_b$) 7.02 (d, J=8.05 Hz, 2H, H$_c$) 5.23 (t, J=5.37 Hz, 2H, —OH) 4.15, 4.05 (dd, J=5.61, 14.1 Hz, 2H, —CH$_2$—) IR (KBr), 3454, 3320, 1656, 1611, 1567, 1542, 1222, 1161, 957, 822 (cm$^{-1}$)

(D) Synthesis of 4,4'-dibromo-biphenyl-2,2'-dicarbaldehyde (4)

To a dry CH$_2$Cl$_2$ (30 mL) are added oxalyl dichloride (1.1 mL, 12.9 mmol) and dimethyl sulfide (2.00 mL, 28.2 mmol) under a nitrogen atmosphere at −78° C. and stirred for 1 hour.

Then, it is added with 4,4'-dibromo-2,2'-bis(methoxycarbonyl)-1,1'-biphenyl (2.10 g, 5.64 mmol) and triethylamine (7.86 mL, 56.4 mmol) and stirred for 2 hours.

The resulting mass is extracted with an ethyl acetate, dried with an anhydrous magnesium sulfate and concentrated. By purifying through the column chromatography (hexane:chloroform=2:1) is obtained 4,4'-dibromo-biphenyl-2,2'-dicarbaldehyde (1.87 g, 5.08 mmol, 90%) as a yellow powder. The thus obtained powder is recrystallized with a mixed solvent of chloroform and hexane to obtain a white plate crystal.

(Characteristics)
$^1$H NMR (CDCl$_3$, 400 MHz) δ (ppm)=9.77 (s, 2H, —CHO) 8.17 (d, J=2.44 Hz, 2H, H$_a$) 7.80 (dd, J=2.44, 8.30 Hz, 2H, H$_b$) 7.21 (d, J=8.30 Hz, 2H, H$_c$) IR (KBr), 1693, 1682, 1583, 1457, 1389, 1179, 1086, 877, 833, 677 (cm$^{-1}$)

(E) Synthesis of 2,7-dibromo-trans-9,10-dihydrophenanthrene-9,10-diol (5)

To a solution of 4,4'-dibromo-biphenyl-2,2'-dicarbaldehyde (2.70 g, 7.33 mmol) dissolved in a dry THF (60 mL) at −78° C. is added titanium(IV) chloride (1.21 mL, 11.0 mmol) dropwise under a nitrogen atmosphere, and after 30 minutes zinc (1.44 g, 22.0 mmol) is added and turned to 0° C. and stirred for 3 hours.

The resulting mass is extracted with an ethyl acetate, dried with an anhydrous magnesium sulfate and concentrated. By purifying through the column chromatography (hexane:ethyl acetate=3:1) is obtained 2,7-dibromo-trans-9,10-dihydrophenanthrene-9,10-diol (2.17 g, 5.86 mmol, 80%) as a white powder. The thus obtained powder is recrystallized with a mixed solvent of chloroform and hexane to obtain a white plate crystal.

(Characteristics)
$^1$H NMR (DMSO-d, 400 MHz) δ (ppm)=7.76 (d, J=8.29 Hz, 2H, H$_a$) 7.71 (dd, J=2.20. 8.29 Hz, 2H, H$_b$) 7.55 (d, J=2.20 Hz, 2H, H$_a$) 5.88 (s, 2H, -benzyl H) 4.47 (s, 2H, —OH) IR (KBr), 3349, 1459, 1416, 1193, 1141, 1084, 1027, 805, 633, 446 (cm$^{-1}$)

Identification of the monomer is performed by an elemental analysis, IR (KBr method) and $^1$H NMR. The characteristics of the thus obtained dihalide are shown below.

|  | C | H | Br | O |
|---|---|---|---|---|
| cal | 45.44 | 2.72 | 43.19 | 8.65 |
| found | 45.32 | 2.83 | 42.96 | 8.91 |

<Identification of Monomer>
Compound 6 in [Formula 17]
(F) Synthesis of 2,7-dibromo-9,10-dihydro-9,10-dimethoxyphenanthrene (6)

To a solution of 2,7-dibromo-9,10-dihydrophenanthrene-9,10-diol (1.54 g, 4.15 mmol) dissolved in a dry THF (20 mL) are added sodium hydride (0.40 g, 16,7 mmol) and iodomethane (1.5 mL, 23.8 mmol) under a nitrogen atmosphere and stirred for 3 hours at room temperature.

The resulting mass is extracted with an ethyl acetate, dried with an anhydrous magnesium sulfate and concentrated. By purifying through the column chromatography (hexane:chloroform=3:1) is obtained 2,7-dibromo-9,10-dihydro-9,10-dimethoxyphenanthrene (1.49 g, 3.74 mmol, 90%) as a white powder. The thus obtained powder is recrystallized with a mixed solvent of chloroform and hexane to obtain a white plate crystal.

Melting point (mp), 150.5-151.5° C. $^1$H NMR (CDCl$_3$, 400 MHz) δ (ppm)=7.61 (d, J=8.05 Hz, 2H, H$_c$) 7.55 (d, J=1.95 Hz, 2H, H$_a$) 7.53 (dd, J=1.95, 8.29 Hz, 2H, H$_b$) 4.32 (s, 2H, -benzyl H) 3.43 (s, 6H, —CH$_3$) IR (KBr), 2933, 2894, 2823, 1469, 1207, 1179, 1097, 1005, 881, 819 (cm$^{-1}$)

| Elemental Analysis | | | | |
|---|---|---|---|---|
|  | C | H | Br | O |
| calculate | 48.27 | 3.54 | 40.14 | 8.04 |
| found | 48.08 | 3.63 | 40.20 | 8.19 |

In FIG. 1 is shown a NMR spectrum of the above Compound 6.

Compound 7 in [Formula 17]
(G) Synthesis of 2,7-dibromo-9,10-dihydro-9,10-bis(trimethylsilyloxy)phenanthrene (7)

To a solution of 2,7-dibromo-9,10-dihydrophenanthrene-9,10-diol (1.43 g, 3.86 mmol) dissolved in a dry THF (5 mL) are added chlorotrimethylsilane (1.5 mL, 11.8 mmol) and triethylamine (5 mL, 35.9 mmol) under a nitrogen atmosphere and stirred for 5 hours under reflux.

The resulting mass is extracted with an ethyl acetate, dried with an anhydrous magnesium sulfate and concentrated. By purifying through the column chromatography (hexane:chloroform=1:1) is obtained 2,7-dibromo-9,10-dihydro-9,10-bis(trimethylsilyloxy)phenanthrene (1.60 g, 3.11 mmol, 81%) as a white powder. The thus obtained powder is recrystallized with a mixed solvent of chloroform and hexane to obtain a white plate crystal.

(Characteristics)
mp 144.0-145.0° C. $^1$H NMR (CDCl$_3$, 400 MHz) δ (ppm), 7.67 (d, J=0.49 Hz, 2H, H$_c$) 7.53-7.30 (dd, J=0.73 Hz, 4H, H$_b$, H$_a$) 4.66 (s, 2H, -benzyl H) 0.28 (s, 18H, —CH$_3$) IR (KBr), 1253, 1190, 1158, 1096, 924, 908, 883, 867, 838, 808 (cm$^{-1}$)

|  | C | H | Br |
|---|---|---|---|
| cal | 46.70 | 5.09 | 31.07 |
| found | 46.48 | 4.75 | 31.65 |

Figure 2:
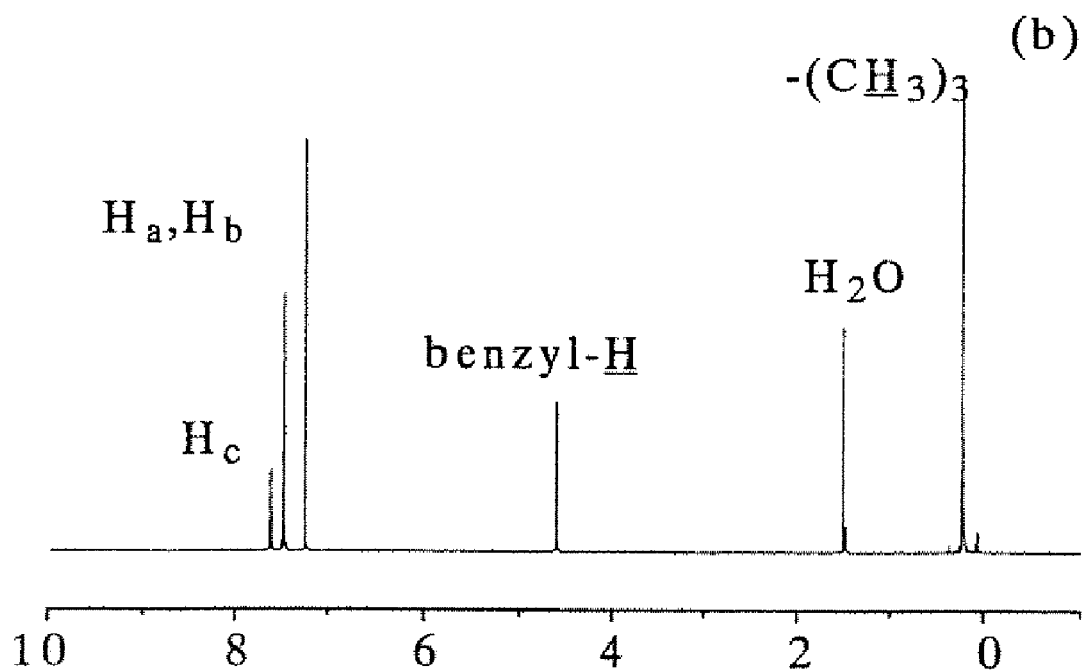
FIG. 2 is a NMR spectrum of a compound 7 in Formula 17.
Figure 3:
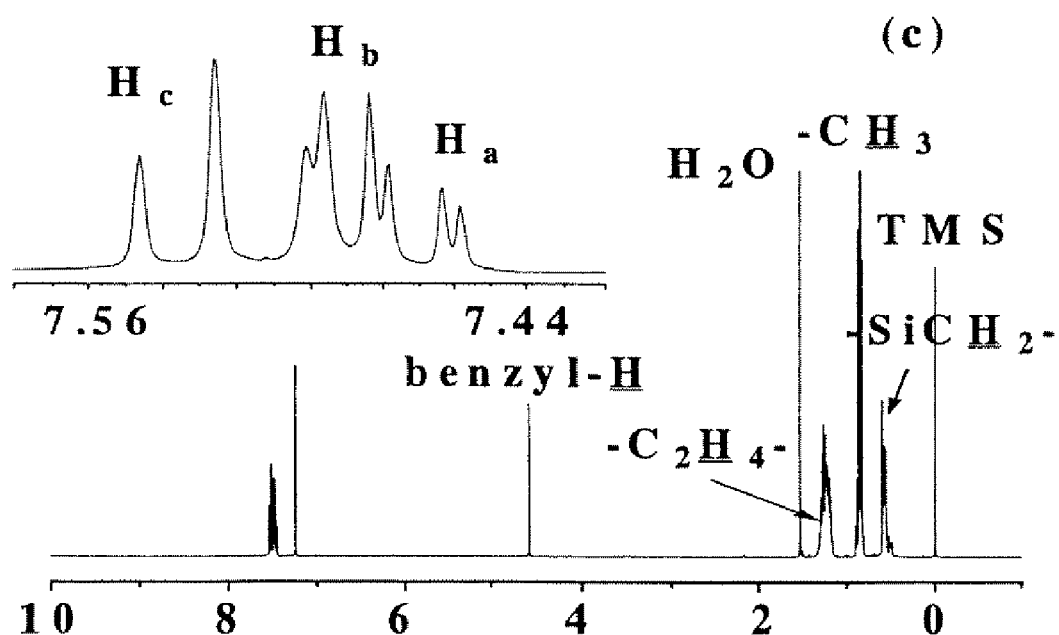
FIG. 3 is a NMR spectrum of a compound 8 in Formula 17.

In FIG. 2 is shown a NMR spectrum of the above Compound 7. In the following description, a NMR spectrum is a 1H-NMR spectrum, and H$_a$-H$_c$ belong to hydrogens bonded with a benzene ring.

Compound 8 in [Formula 17]
(H) Synthesis of 2,7-dibromo-trans-9,10-dihydro-9,10-bis(tributylsilyloxy)phenanthrene (8)

To a solution of 2,7-dibromo-trans-9,10-dihydrophenanthrene-9,10-diol (1.88 g, 5.08 mmol) dissolved in a dry THF (30 mL) are added chlorotributylsilane (3.0 mL, 11.2 mmol) and 1,8-diazabicyclo[5.4.0.]-7-undecene (1.9 mL, 12.7 mmol) under a nitrogen atmosphere and stirred for 5 hours at room temperature.

The resulting mass is extracted with an ethyl acetate, dried with an anhydrous magnesium sulfate and concentrated. By purifying through the column chromatography (hexane:chloroform=1:4) is obtained 2,7-dibromo-trans-9,10-dihydro-9,10-bis(tributylsilyloxy)phenanthrene (3.7 g, 4.83 mmol, 95%) as a white oil.

(Characteristics)
Oil
$^1$H NMR (CDCl$_3$, 400 MHz) δ (ppm), 7.54 (d, J=8.05 Hz, 2H, H$_c$) 7.49 (dd, J=2.20, 7.09 Hz, 2H, H$_b$) 7.46 (d, J=2.30 Hz 2H, H$_a$) 4.56 (s, 2H, -benzyl H) 1.30-1.18 (m, 24H, —CH$_2$CH$_2$—) 0.85 (t, J=6.83, 7.32 Hz, 18H, —CH$_3$) 0.60-0.56 (b, 12H, —SiCH$_2$—) IR (KBr), 2956, 2923, 2871, 1464, 1195, 1082, 1005, 906, 886, 812 (cm$^{-1}$)

|      | C     | H    | Br    |
|------|-------|------|-------|
| cal  | 59.51 | 8.15 | 20.84 |
| found| 59.80 | 7.96 | 19.64 |

Figure 8:
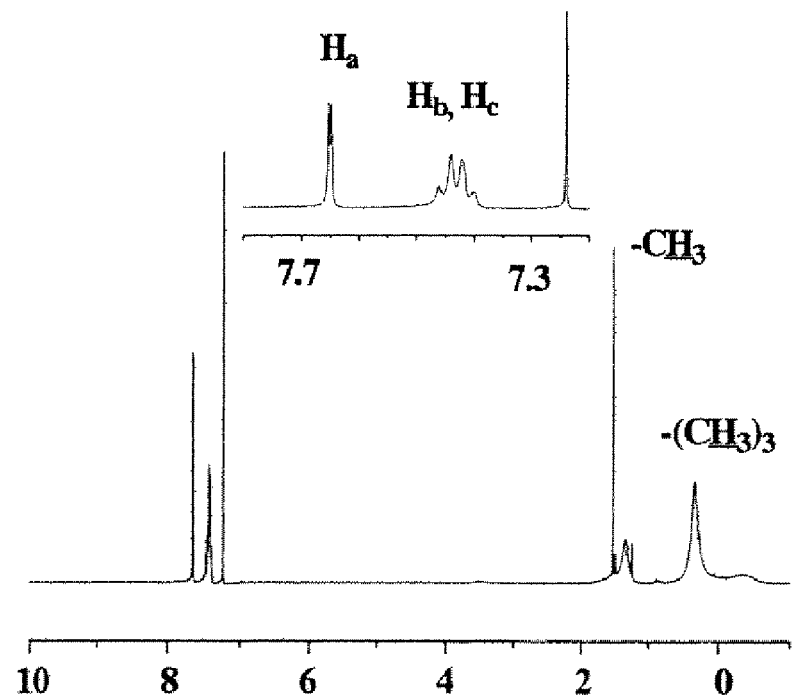
FIG. 8 is a NMR spectrum of a compound 16 in Formula 19.

In FIG. 8 is shown a NMR spectrum of the above Compound 8.

Compound 9 in [Formula 17]

(I) Synthesis of 2,7-dibromo-trans-9,10-dihydro-9,10-bis(tert-butyldimethylsilyloxy)phenanthrene (9)

To a solution of 2,7-dibromo-trans-9,10-dihydrophenanthrene-9,10-diol (0.94 g, 2.54 mmol) dissolved in a dry THF (15 mL) are added tert-butyldimethylsilane (1.91 g, 12.7 mmol) and 1,8-diazabicyclo[5.4.0.]-7-undecene (2.3 mL, 15.4 mmol) under a nitrogen atmosphere and stirred for 14 hours at room temperature.

The resulting mass is extracted with an ethyl acetate, dried with an anhydrous magnesium sulfate and concentrated. By purifying through the column chromatography (hexane:chloroform=1:1) is obtained 2,7-dibromo-trans-9,10-dihydro-9,10-bis(tert-butyldimethylsilyloxy)phenanthrene (1.35 g, 2.26 mmol, 89%) as a white powder. The thus obtained powder is recrystallized with a mixed solvent of chloroform and hexane to obtain a white plate crystal.

(Characteristics)

mp 162.0-163.0° C.

$^1$H NMR (CDCl$_3$, 400 MHz) δ (ppm)=7.57-7.46 (m, 6H, H$_a$, H$_b$, H$_c$) 4.57 (s, 2H, -benzyl-H) 0.85 (s, 18H, —C(CH$_3$)$_3$) 0.14-0.06 (s, 12H, —Si(CH$_3$)$_2$) IR (KBr), 2953, 2928, 1471, 1257, 1083, 910, 845, 837, 814, 775 (cm$^{-1}$)

|      | C     | H    | Br    |
|------|-------|------|-------|
| cal  | 52.17 | 6.40 | 26.70 |
| found| 52.21 | 6.37 | 27.00 |

Figure 4:
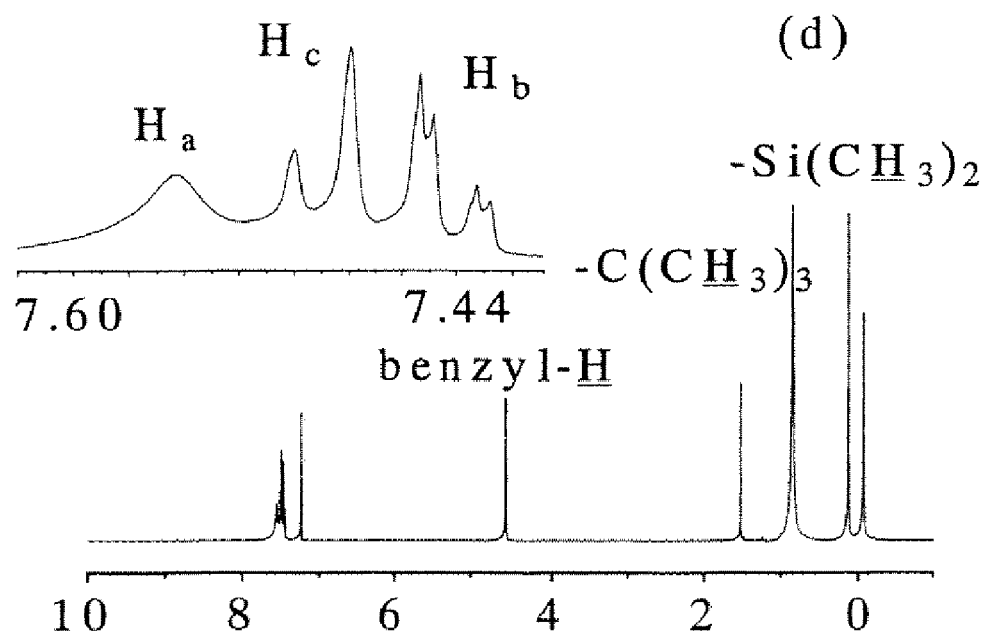
FIG. 4 is a NMR spectrum of a compound 9 in Formula 17.

In FIG. 4 is shown a NMR spectrum of the above Compound 9.

Compound 10 in [Formula 17]

(J) Synthesis of 2,7-dibromo-trans-9,10-dihydro-9,10-bis(dimethylphenylsilyloxy)phenanthrene (10)

To a solution of 2,7-dibromo-trans-9,10-dihydrophenanthrene-9,10-diol (0.70 g, 1.89 mmol) dissolved in a dry THF (10 mL) are added chlorodimethylphenylsilane (1 mL, 5.96 mmol) and 1,8-diazabicyclo[5.4.0.]-7-undecene (1.7 mL, 11.4 mmol) under a nitrogen atmosphere and stirred for 3 hours at room temperature.

The resulting mass is extracted with an ethyl acetate, dried with an anhydrous magnesium sulfate and concentrated. By purifying through the column chromatography (hexane:chloroform=5:1) is obtained 2,7-dibromo-trans-9,10-dihydro-9,10-bis(dimethylphenylsilyloxy)phenanthrene (0.79 g, 1.24 mmol, 65%) as a white solid.

(Characteristics)

mp 103.0-104.0° C. $^1$H NMR (CDCl$_3$, 400 MHz) δ (ppm)=7.52-7.34 (m, 16H, H$_a$, H$_b$, H$_c$, -Ph) 4.61 (s, 2H, -benzyl H) 0.35, 0.32 (s, 12H, —CH$_3$) IR (KBr), 1254, 1117, 1053, 912, 866, 845, 826, 786, 736, 698 (cm$^{-1}$)

Figure 5:
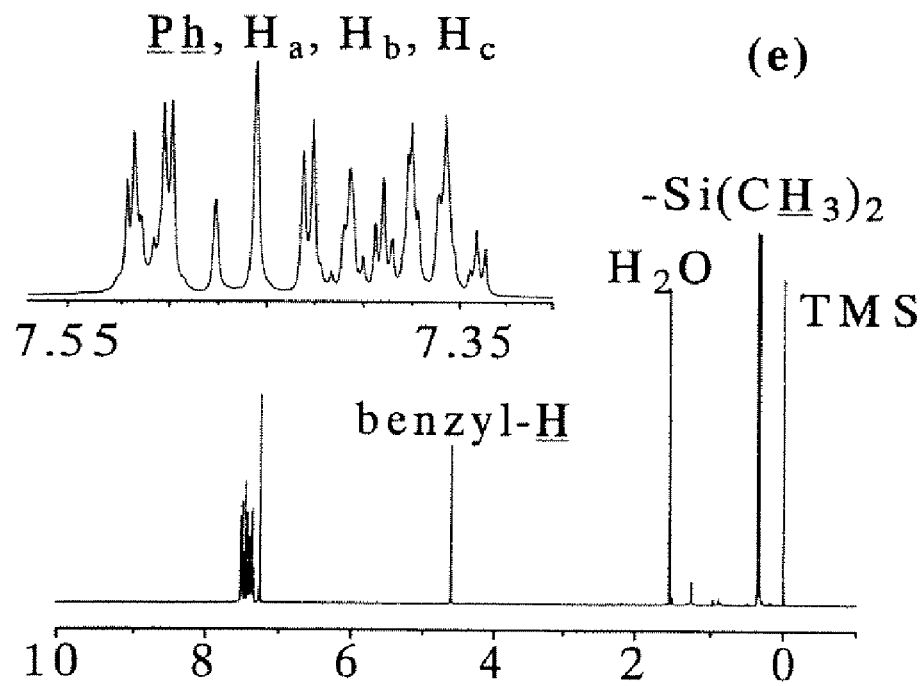
FIG. 5 is a NMR spectrum of a compound 10 in Formula 17.

In FIG. 5 is shown a NMR spectrum of the above Compound 10.

Compound 11 in [Formula 17]

(K) Synthesis of 2,7-dibromo-trans-9,10-dihydro-9,10-bis(dimethyloctadecylsilyloxy)phenanthrene (11)

To a solution of 2,7-dibromo-trans-9,10-dihydrophenanthrene-9,10-diol (1.19 g, 3.22 mmol) dissolved in a dry THF (20 mL) are added chlorodimethyloctadecylsilane (4.47 g, 12.9 mmol) and 1,8-diazabicyclo[5.4.0.]-7-undecene (2.4 mL, 16.0 mmol) under a nitrogen atmosphere and refluxed for 5 hours.

The resulting mass is extracted with an ethyl acetate, dried with an anhydrous magnesium sulfate and concentrated. By purifying through the column chromatography (hexane:chloroform=5:1) is obtained 2,7-dibromo-trans-9,10-dihydro-9,10-bis(dimethyloctadecylsilyloxy)phenanthrene (1.81 g, 1.83 mmol, 57%) as a white solid.

(Characteristics)

mp 51.5-52.5° C. $^1$H NMR (CDCl$_3$, 400 MHz) δ (ppm)= 7.60, 7.47 (s, 6H, H$_a$, H$_b$, H$_c$) 4.57 (s, 2H, -benzyl H) 1.24 (br, 64H, —CH$_2$—) 0.86 (t, 6H, —CH$_3$) 0.69 (t, 4H, —SiCH$_2$—) 0.18, 0.15 (s, 12H, —Si(CH$_3$)$_3$) IR (KBr), 2955, 2917, 2850, 1471, 1253, 1192, 1158, 1098, 856, 809 (cm$^{-1}$)

|      | C     | H    | Br    |
|------|-------|------|-------|
| cal  | 65.43 | 9.56 | 16.12 |
| found| 65.44 | 9.38 | 16.28 |

Figure 6:
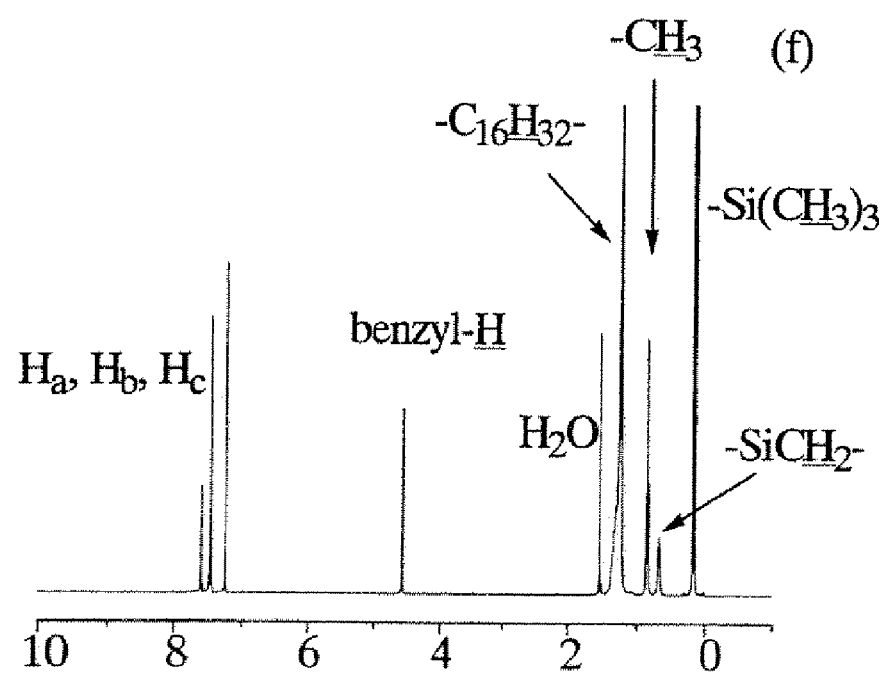
FIG. 6 is a NMR spectrum of a compound 11 in Formula 17.

In FIG. 6 is shown a NMR spectrum of the above Compound 11.

Example 2

Then, the synthesis of a polymer is tried by using the dihalides obtained as mentioned above as a starting material. That is, the synthesis of the polymer compound according to the invention is tried by polycondensation of a dihalide of 9,10-dihydrophenanthrene having a substituent as a starting material.

A simplified synthesis procedure example is shown below.

[Formula 18]

(A) Polymerization of Homopolymer

The polymerization of 18-SiBu$_3$ is shown as an example.

To bis(1,5-cyclooctadiene)nickel(0) (0.60 g, 2.18 mmol) are added dry DMF (15.0 mL), bipyridine (0.34 g, 2.18 mmol) and 1,5-cyclooctadiene (267 µm, 2.18 mmol) under a nitrogen atmosphere, further added a solution of 2,7-dibromo-trans-9,10-dihydro-9,10-bis(tributylsilyloxy)phenanthrene (0.75 g, 0.98 mmol) in dry DMF (5 mL) and stirred at 60° C. for 4 days.

The resulting solution is quenched with hydrobromic acid, reprecipitated twice with methanol and EDTA-4Na aq and dried to obtain a polymer (0.58 g, 0.96 mmol, 96%) as a blue solid.

The characteristics of the thus obtained polymer are shown in the following Table 1.

TABLE 1

| run | R | Solvent | Time day | Yield % | Polymer | Number average molecular weight (Mn[a]) | Dispersity (Mw/Mn[a]) |
|---|---|---|---|---|---|---|---|
| 1 | $CH_3$ | DMF | 2 d | 98 | 17 | 1,100[b] | 1.2[b] |
| 2 | $SiBu_3$ | DMF | 4 d | 96 | 18 | 9,800 | 2.0 |
| 3 | $Si(CH_3)_2C(CH_3)_3$ | Toluene/DMF 7:3 | 4 d | 95 | 19 | 3,500[b] | 1.1[b] |
| 4 | $Si(CH_3)_2Ph$ | DMF | 4 d | 50 | 20 | 1,300[b] | 1.2[b] |
| 5 | $Si(CH_3)_2(CH_2)_{17}CH_3$ | Toluene/DMF 7:3 | 4 d | 4 d | 21 | 69,000 | 3.0 |

The characteristics of the resulting polymers are as follows. At first, as to the solubility, the polymers in runs 2 and 5 of Table 1 and in formula 22 (paragraph number [0070]) of [Formula 20] are soluble in chloroform, THF and toluene, and the polymers in runs 1, 3 and 4 are slightly soluble in chloroform.

As to the data of fluorescence, run 2 shows emissions at $\lambda_{EX}$ (excitation wavelength)=379 nm and $\lambda_{EM}$ (emission wavelength)=414 nm in a chloroform solution, and shows emissions at $\lambda_{EX}$ (excitation wavelength)=391 nm and $\lambda_{EM}$ (emission wavelength)=431 nm as a film.

Run 5 shows emissions at $\lambda_{EX}$ (excitation wavelength) 398 nm and $\lambda_{EM}$ (emission wavelength)=427 nm in a chloroform solution, and shows emissions at $\lambda_{EX}$ (excitation wavelength)= 398 nm and $\lambda_{EM}$ (emission wavelength)=430 nm as a film.

The formula 22 of [Formula 20] shows emissions at $\lambda_{EX}$ (excitation wavelength)=385 nm and $\lambda_{EM}$ (emission wavelength)=418 nm in a chloroform solution, and shows emissions at $\lambda_{EX}$ (excitation wavelength)=382 nm and $\lambda_{EM}$ (emission wavelength)=432 nm as a film.

As to CV, run 2 shows an oxidation wave at 1.33 V. Run 5 shows an oxidation wave at 1.34 V. Run 6 shows an oxidation wave at 1.16 V. CV means an oxidation wave of a polymer film in a cyclic voltammetry (CV). Moreover, values such as voltage of 1.33V and so on are values corresponding to $Ag^+/Ag$.

As to the heat resistance, the temperature of 5% weight reduction shows 390° C. in run 2, 360° C. in run 5, and 400° C. in the formula 22 of [Formula 20], from which it is understood that the thermal stability is high.

Example 3

Then, a reaction scheme of a dihalide according to the invention in another embodiment is shown below.

[Formula 19]

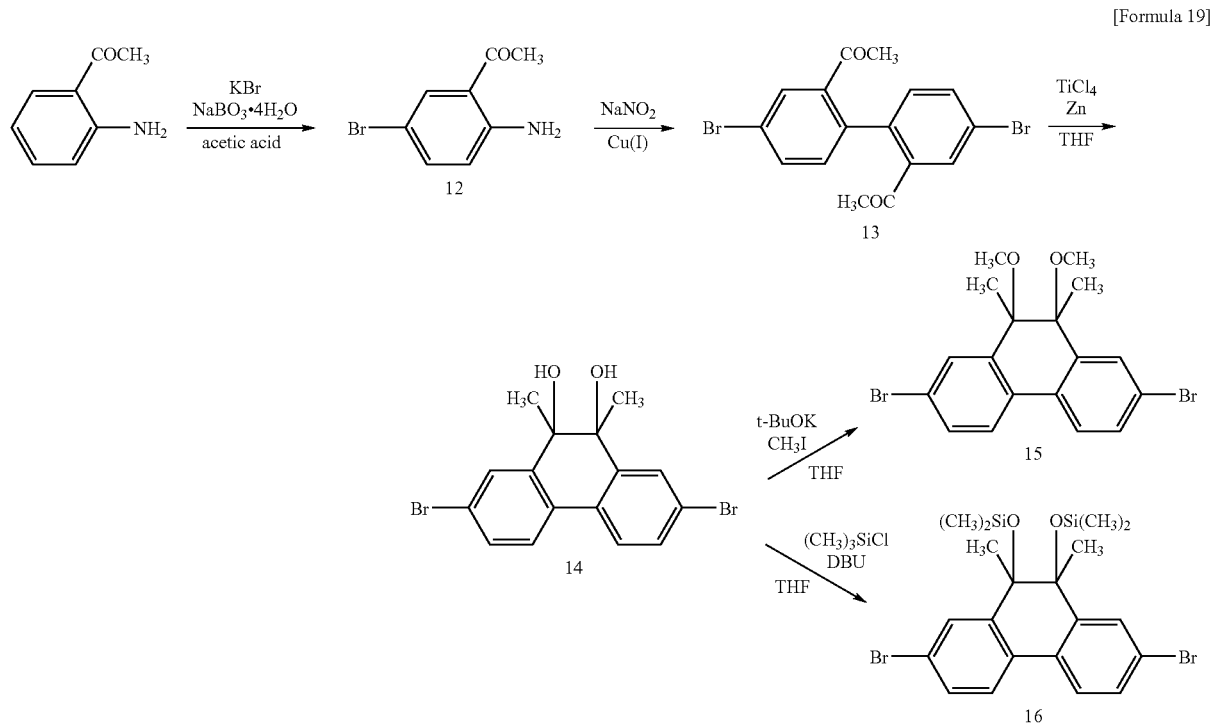

(L) Synthesis of 2-amino-5-bromoacetophenone (12)

To 2-aminoacetophenone (20.0 g, 148 mmol) and potassium bromide (21.2 g, 178 mmol) is added AcOH (60 mL) under a nitrogen atmosphere, which is cooled to 0° C. and added with sodium peroxoborate tetrahydrate (27.3 g, 178 mmol) and stirred for 2 days.

The resulting mass is extracted with a chloroform, dried with an anhydrous magnesium sulfate and concentrated. By purifying through the column chromatography (hexane:chloroform=1:1) is obtained 2-amino-5-bromoacetophenone (27.4 g, 128 mmol, 86%) as a yellow powder. The thus obtained powder is recrystallized with a mixed solvent of chloroform and hexane to obtain a yellow needle-like crystal.

(Characteristics)

$^1$H NMR (CDCl$_3$, 400 MHz) δ (ppm)=7.80 (d, J=2.44 Hz, 1H, H$_a$) 7.32 (dd, J=1.95, 8.79 Hz, 1H, H$_b$) 6.56 (d, J=8.79 Hz, 1H, H$_c$) 6.29 (s, 2H, —NH$_2$) 2.56 (s, 3H, —OCH$_3$) IR (KBr), 3314, 1469, 1394, 1186, 1089, 1036, 1004, 847, 816, 518 (cm$^{-1}$)

(M) Synthesis of 1-(2'-acetyl-4,4'-dibromo-biphenyl-2-yl)etanone (13)

To 2-Amino-5-bromoacetophenone (17.4 g, 81.0 mmol) are added H$_2$O (28 mL) and hydrochloric acid (24 mL), which is cooled to 0° C., further added with sodium nitrite (6.71 g, 97.2 mmol) and stirred for 1 hour. Then, a solution of copper (II) sulfate pentahydrate (40.5 g, 162 mmol) dissolved in H$_2$O (140 mL) and added with 30% of ammonia solution (70 mL) is added with a solution of hydroxyammonium chloride (12.0 g, 178 mmol) in 6N-sodium hydroxide (30 mL) at 0° C. and stirred. To this solution is added dropwise a diazotized solution from below a liquid level of the copper solution over 30 minutes. The resulting solution is turned to a room temperature and stirred for 2 hours. Thereafter, it is heated for 1 hour.

After the solution is acidified with hydrochloric acid, it is extracted with a chloroform, dried with an anhydrous magnesium sulfate and concentrated. By purifying through the column chromatography (silica, hexane:chloroform=1:1) is obtained 1-(2'-acetyl-4,4'-dibromo-biphenyl-2-yl)etanone (16,0 g, 40.4 mmol, 99%) as a yellow powder. The thus obtained powder is recrystallized with a mixed solvent of chloroform and hexane to obtain a white plate crystal.

(Characteristics)

$^1$H NMR (CDCl$_3$, 400 MHz) δ (ppm)=7.86 (d, J=2.44 Hz, 2H, H$_a$) 7.62 (dd, J=1.95, 8.00 Hz, 2H, H$_b$) 7.01 (d, J=8.00 Hz, 2H, H$_c$) 2.33 (s, 6H, —OCH$_3$)

(N) Synthesis of 2,7-dibromo-trans-9,10-dimethylphenanthrene-9,10-diol (14)

To a solution of 1-(2'-acetyl-4,4'-dibromo-biphenyl-2-yl)etanone (10.7 g, 27.0 mmol) dissolved in dry THF (150 mL) is added dropwise titanium(IV) chloride (4.44 mL, 40.5 mmol) under a nitrogen atmosphere, which is added with zinc (5.29 g, 80.9 mmol) after 30 minutes, turned to 0° C. and stirred for 3 hours.

The resulting mass is extracted with an ethyl acetate, dried with an anhydrous magnesium sulfate and concentrated. By purifying through the column chromatography (hexane:ethyl acetate=3:1) is obtained 2,7-dibromo-trans-9,10-dimethylphenanthrene-9,10-diol (9.57 g, 24.0 mmol, 89%) as a yellow solid.

(Characteristics)

$^1$H NMR (CDCl$_3$, 400 MHz) δ (ppm)=7.85 (d, J=1.95 Hz, 2H, H$_a$) 7.51 (d, J=8.30 Hz, 2H, H$_c$) 7.46 (dd, J=1.95, 8.30 Hz, 2H, H$_b$) 2.50 (s, 2H, —OH) 1.30 (s, 6H, —CH$_3$) IR (KBr), 3447, 1463, 1365, 1178, 1096, 1056, 950, 930, 809, 685 (cm$^{-1}$)

The identification of the monomer is performed by an elemental analysis, IR (KBr method) and $^1$H NMR. The characteristics of the dihalide thus obtained are shown below.

Compound 15 in [Formula 19]

(O) Synthesis of 2,7-dibromo-trans-9,10-dimethoxy-9,10-dimethylphenanthrene (15)

To a solution of 2,7-dibromo-trans-9,10-dimethylphenanthrene-9,10-diol (2.71 g, 6.81 mmol) dissolved in dry THF (20 mL) is added potassium tert-butoxide (3.28 g, 29.2 mmol) under a nitrogen atmosphere and stirred at room temperature for 3 hours. Then, it is added with iodomethane (6.00 mL, 96.4 mmol) and stirred under reflux for 4 days.

The resulting mass is extracted with a chloroform and a sodium thiosulfate, dried with an anhydrous magnesium sulfate and concentrated. By purifying through the column chromatography (hexane:chloroform=3:1) is obtained 2,7-dibromo-trans-9,10-dimethoxy-9,10-dimethylphenanthrene (0.50 g, 1.17 mmol, 17%) as a white powder. The thus obtained powder is recrystallized with a mixed solvent of chloroform and hexane to obtain a white plate crystal.

(Characteristics)

mp 202.5-203.0° C. $^1$H NMR (DMSO-d, 400 MHz) δ (ppm)=7.77 (d, J=8.30 Hz, 2H, H$_c$) 7.66 (d, J=2.20 Hz, 2H, H$_a$) 7.57 (dd, J=1.95, 8.29 Hz, 2H, H$_b$) 3.29 (s, 6H, —OCH$_3$) 1.54 (s, 6H, —CH$_3$) IR (KBr), 1476, 1461, 1250, 1206, 1118, 1078, 1037, 1004, 810, 795 (cm$^{-1}$)

|  | C | H | Br | O |
|---|---|---|---|---|
| cal | 50.73 | 4.26 | 37.50 | 7.51 |
| found | 50.45 | 4.13 | 37.18 | 7.52 |

Figure 7:
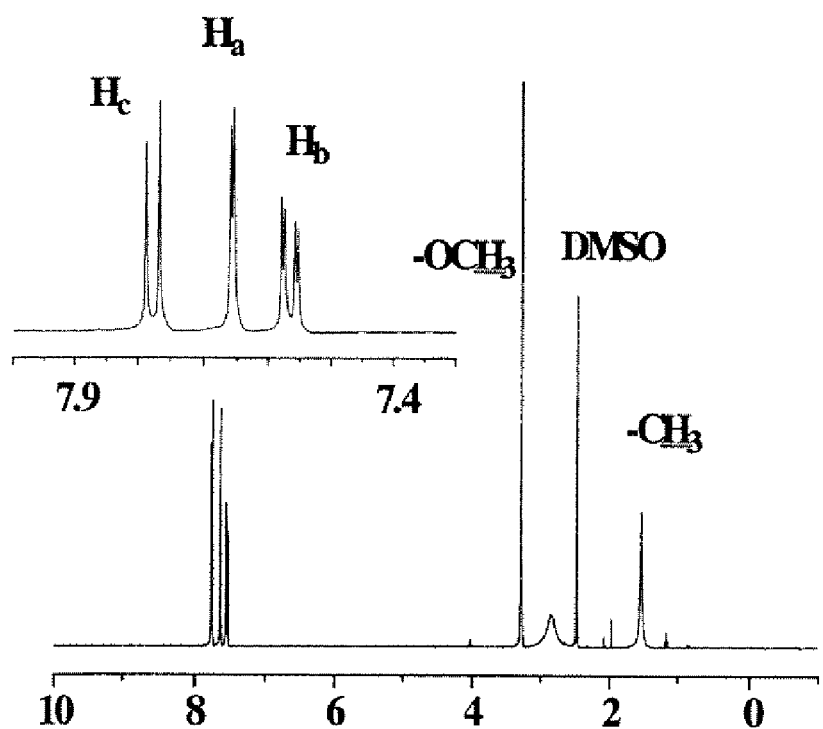
FIG. 7 is a NMR spectrum of a compound 15 in Formula 19.

In FIG. 7 is shown a NMR spectrum of the above compound 15.

Compound 16 in [Formula 19]

(P) Synthesis of 2,7-dibromo-trans-9,10-dimethyl-9,10-Bis(trimethylsilyloxy)phenanthrene (16)

To a solution of 2,7-dibromo-trans-9,10-dimethylphenanthrene-9,10-diol (3.50 g, 8.79 mmol) dissolved in dry THF (30 mL) are added chlorotrimethylsilane (4.46 mL, 35.1 mmol) and 1,8-diazabicyclo[5.4.0.]-7-undecene (10 mL, 71.7 mmol) under a nitrogen atmosphere and stirred under reflux for 7 hours.

The resulting mass is extracted with an ethyl acetate, dried with an anhydrous magnesium sulfate and concentrated. By purifying through the column chromatography (hexane:chloroform=3:1) is obtained 2,7-dibromo-trans-9,10-dimethyl-9,10-bis(trimethylsilyloxy)phenanthrene (3.93 g, 7.24 mmol, 82%) as a white powder. The thus obtained powder is recrystallized with a mixed solvent of chloroform and hexane to obtain a white plate crystal.

(Characteristics)

mp 140.0-141.0° C. $^1$H NMR (CDCl$_3$, 400 MHz) δ (ppm)= 7.65 (d, J=1.71Hz, 2H, H$_a$) 7.40-7.46 (m, 4H, H$_b$, H$_c$) 1.34 (s, 6H, —CH$_3$) 0.33 (s, 18H, —(CH$_3$)$_3$) IR (KBr), 1264, 1252, 1219, 1155, 1114, 1070, 1019, 888, 861, 839 (cm$^{-1}$)

In FIG. 8 is shown a NMR spectrum of the above compound 16.

Example 4

Then, the synthesis of a polymer is tried by using the above-obtained dihalides as a starting material. That is, the synthesis of the polymer compound according to the invention is tried by polycondensing a dihalide of 9,10-dihydrophenanthrene having a substituent as a starting material.

The simplified synthesis procedure of the hompolymer is shown below.

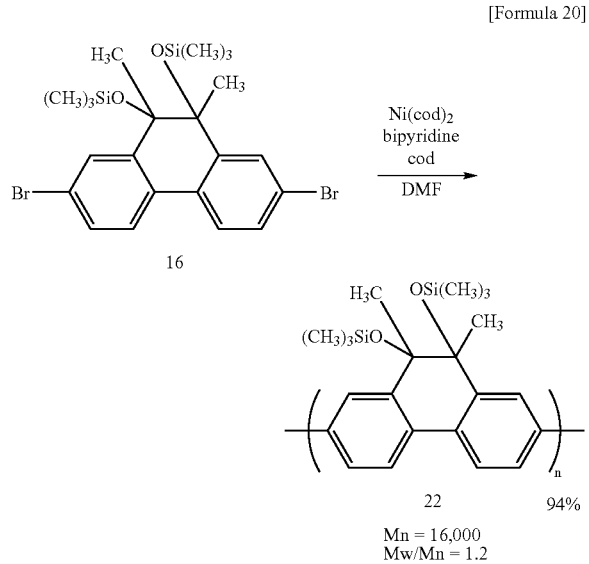

[Formula 20]

(Procedure)

To bis(1,5-cyclooctadiene)nickel(0) (0.51 g, 1.84 mmol) are added dry DMF (15.0 mL), bipyridine (0.30 g, 1.92 mmol), 1,5-cyclooctadiene (226 μL, 1.84 mmol) and 2,7-dibromo-trans-9,10-dimethyl-9,10-bis(trimethylsilyloxy) phenanthrene (0.50 g, 0.92 mmol) and stirred at 60° C. for 4 days.

The resulting solution is quenched with hydrobromic acid, reprecipitated with methanol and EDTA-4Na aq and dried to obtain a polymer 22 (0.33 g, 0.86 mmol, 94%) as a yellow powder.

Similarly, the copolymerization can be performed by using a monomer represented in Formula 17 or 20.

(A) Copolymerization by Sonogashira Reaction

A synthesis of 27 is shown as an example.

To 2,7-Dibromo-trans-9,10-dihydoro-9,10-dimethoxyphenanthrene (0.39 g, 0.98 mmol) are added dry THE (25 mL), tetrakis(triphenylphosphine)palladium(0) (56.6 mg, 49.0 μmol), copper(I) iodide (10.0 mg, 52.5 μmol), triethylamine (10 mL, 71.7 mmol) and 2,7-diethynyl-9,9-dioctylfluorene (0.43 g, 0.98 mmol) in turn and stirred at 60° C. for 4 days.

The resulting solution is reprecipitated with methanol and EDTA-4Na aq and dried to obtain a polymer (0.65 g, 0.96 mmol. 98%) as a yellow powder.

(B) Copolymerization by Suzuki Reaction

A synthesis of 31 is shown as an example,

To tetrakis(triphenylphosphine)palladium(0) (58.0 mg, 0.05 mol) is added toluene (20 mL) bubbled with nitrogen and further added 9,9-dioctylfluorene-2,7-bis(trimethyleneborate) (0.56 g, 1.00 mmol), 2,7-dibromo-trans-9,10-dimethoxyl-9,10-dimethylphenanthrene (0.43 g, 1.00 mmol), 2 M of bubbled potassium carbonate (5.0 mL) and methanol (5.0 mL) and stirred at 80° C. for 4 days.

The resulting solution is reprecipitated with methanol and EDTA-4Na aq and dried to obtain a polymer (0.65 g, 1.00 mmol, 99%) as a green powder.

Characteristics of the polymers obtained in the above (A) and (B) are shown in the following Table 2.

TABLE 2

| | Time h | Yield % | Polymer | Number average molecular weight (Mn$^a$) | Dispersity (Mw/Mn$^a$) |
|---|---|---|---|---|---|
| ![structure with R⁴=CH₃, R⁵=n-C₈H₁₇] R⁴ = CH₃, R⁵ = n-C₈H₁₇ | 4 d | 98 | 27 | 7000 | 3.0 |
| ![structure with R⁶=Si(n-C₄H₉)₃, R⁷=n-C₁₂H₂₅] R⁶ = Si(n-C₄H₉)₃, R⁷ = n-C₁₂H₂₅ | 4 d | 98 | 28 | 8500 2300 | 2.4 1.1 |

TABLE 2-continued

| Polymer | Time h | Yield % | Polymer | Number average molecular weight (Mn[a]) | Dispersity (Mw/Mn[a]) |
|---|---|---|---|---|---|
| 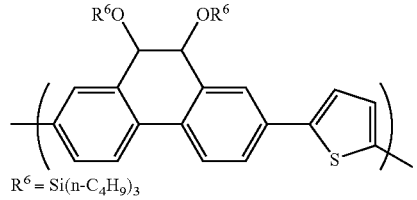 R[6] = Si(n-C$_4$H$_9$)$_3$ | 4 d | 96 | 29 | 3100 | 1.3 |
| 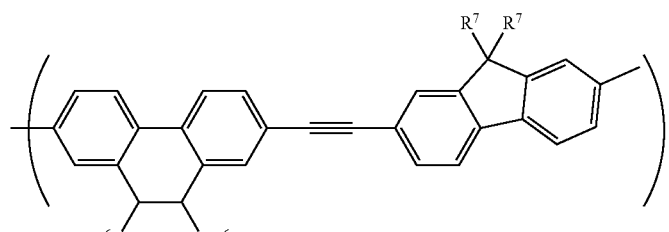 R[6] = Si(n-C$_4$H$_9$)$_3$, R[7] = n-C$_8$H$_{17}$ | 4 d | 97 | 30 | 6600 | 2.2 |
| 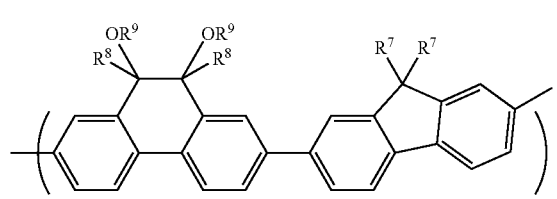 R[7] = n-C$_8$H$_{17}$, R[8] = CH$_3$, R[9] = CH$_3$ | 4 d | 98 | 31 | 21000 | 2.4 |

[a]Determined by GPC (elueut:CHCl$_3$)

Each of the homopolymers and copolymers obtained according to the invention is dissolved in an organic solvent such as chloroform or the like, and the resulting solution is applied onto a glass or a metal plate of platinum or the like and dried at room temperature in air to obtain a polymer thin film. The resulting thin film has a strength durable to a visible-ultraviolet fluorescence spectroscopy and an electrochemical measurement. Also, the deterioration is not observed even if the thin film is left to stand in air.

The homopolymer (22) is mentioned as an example.

The solution of the polymer in chloroform (about $1.5 \times 10^{-5}$M) is applied over a full surface of a nonfluorescent glass (2 cm×5 cm) and then dried at room temperature in air to obtain an uniform thin film. As a fluorescence spectrum of the filmed polymer is measured (excitation wavelength 382 nm), an emission peak is observed at 432 and 454 nm.

Example 5

Then, ultraviolet spectrum and fluorescence spectrum are measured to the polymer compounds of the invention obtained in Examples 2 and 4. The results are shown in Tables 3 and 4.

Table 3 shows optical characteristics of the homopolymer.

TABLE 3

(Optical characteristics of Homopolymer)

| run | Polymer | Absorbance $\lambda_{max}$/nm CHCl$_3$ soln. | film | Fluorescence ($\lambda_{max}$ (EX/nm)) CHCl$_3$ soln. | film | $\lambda_{max}$ (EM)/nm Quantum yield Φ (%) |
|---|---|---|---|---|---|---|
| 1 | 17-CH3 | 351 |  | 410 (361) |  | 89 |
| 2 | 18-SiBu$_3$ | 378 | 392, 415 | 414, 438 (379) | 431, 456, 486 (391) | 100 |
| 3 | 19-Si(CH$_3$)$_2$C(CH$_3$)$_3$ | 382 | 384 | 415 (373) | 434, 457, 486 (370) | 82 |
| 4 | 20-Si(CH$_3$)$_2$Ph | 367 |  | 412, 434 (367) |  | 86 |

TABLE 3-continued (Optical characteristics of Homopolymer)

| run | Polymer | Absorbance $\lambda_{max}$/nm | | Fluorescence $\lambda_{max}$ (EM)/nm ($\lambda_{max}$ (EX/nm)) | | $\lambda_{max}$ (EM)/nm Quantum yield |
|---|---|---|---|---|---|---|
| | | CHCl$_3$ soln. | film | CHCl$_3$ soln. | film | Φ (%) |
| 5 | 21-Si(CH$_3$)$_2$(CH$_2$)$_{17}$CH$_3$ | 410 | 393, 411 | 427, 454 (398) | 430, 456 (398) | 62 |
| 6 | 22-Si(CH$_3$)$_3$—CH$_3$ | 382 | 392 | 418, 440 (385) | 432, 454 (382) | 100 |

Table 4 shows optical characteristics of the copolymer.

TABLE 4

(Optical characteristics of Copolymer)

| num | Polymer | Absorbance $\lambda_{max}$/nm | | Fluorescence $\lambda_{max}$ (EM)/nm ($\lambda_{max}$ (EX/nm)) | | Quantum yield |
|---|---|---|---|---|---|---|
| | | CHCl$_3$ soln. | film | CHCl$_3$ soln. | film | Φ (%) |
| 1 | 27-CH$_3$-FL-Acelyl | 390, 408 | 397, 421 | 423, 447 (410) | 480, 508 (436) | 82 |
| 2 | 28-SiBu$_3$-Ph-Acetyl | 333, 386 | 333, 387 | 441 (333, 397) | 517 (398) | 53 |
| 3 | 29-SiBu$_3$-Thiophene | 405 | 404 | 464, 485 (412) | 480, 506 (399) | 89 |
| 4 | 30-SiBu$_3$-FL | 377 | 382 | 416, 439 (378) | 428, 453 (378) | 89 |
| 5 | 31-CH$_3$—CH$_3$-FL | 387 | 382 | 418, 443 (383) | 428, 453 (371) | 84 |

These results show absorption points of light from the visible-ultraviolet absorption spectrum, from which it is found that the polymer can be used for a coloring material about the absorption at a visible portion and an ultraviolet light absorber. Moreover, since emission is observed in the emission spectrum (fluorescence spectrum), it is found that the polymer can be used in a fluorescent paint or the like.

Since the polymer compound according to the invention shows the solubility in an organic solvent such as chloroform or the like, it is easy to apply the solution of the polymer compound onto a substrate such as glass or the like.

INDUSTRIAL APPLICABILITY

According to the invention, there can be provided a functional material or the like having a solubility, an electrochemical activity, a fluorescence, a heat resistance and so on, so that the invention can widely contribute to optical and electrochemical field.

The invention claimed is:

1. A dihalide represented by the following formula:

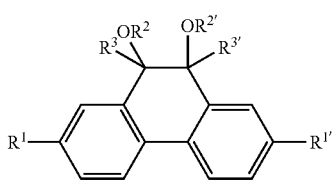

[Formula 1]

(wherein $R^1$ and $R^{1'}$ represent a halogen, $R^2$ and $R^{2'}$ represent a silyl group having a substituent, and $R^3$ and $R^{3'}$ represent a hydrogen or an alkyl group).

2. The dihalide group according to claim 1, wherein the silyl group having the substituent is at least one selected from the group consisting of Si(CH$_3$)$_3$,Si(n-C$_4$H$_9$)$_3$,Si(t-C$_4$H$_9$)$_3$,Si(CH$_3$)$_2$(C$_6$H$_5$) and Si(CH$_3$)$_2$(n-C$_{18}$H$_{37}$).

3. The dihalide according to claim 1 or 2 wherein the alkyl group is an alkyl group having a carbon number of 1-20.

4. A polymer compound having a structure represented by the following formula in its main chain:

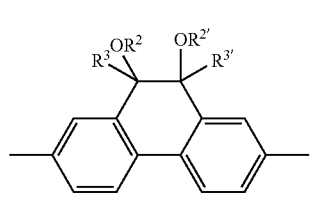

[Formula 2]

wherein $R^2$ and $R^{2'}$ represent a silyl group having a substitute, and $R^3$ and $R^{3'}$ represent a hydrogen or an alkyl group).

5. The polymer compound according to claim 4, which is represented by the following formula:

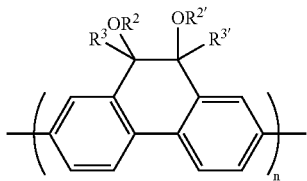

(wherein $R^2$ and $R^{2'}$ represent a silyl group having a substituent, and $R^3$ and $R^{3'}$ represent a hydrogen or an alkyl group, and n represents a polymerization degree and is 5-1000).

6. The polymer compound according to claim 4, which is a copolymer comprising the structure represented by the formula claimed in claim 4 and another structure.

7. The polymer compound according to claim 5 wherein the copolymer is at least one selected from the group consisting of the following formulae:

[Formula 4]

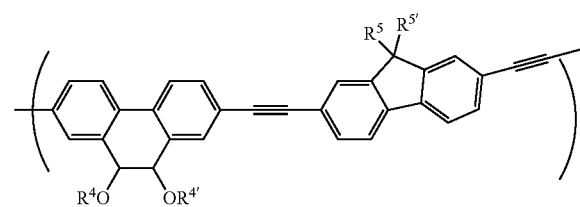

(wherein $R^4$, $R^{4'}$, $R^5$ and $R^{5'}$ represent an alkyl group),

[Formula 5]

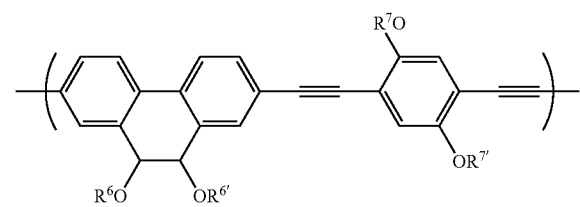

(wherein $R^6$ and $R^{6'}$ represent a silyl group having a substituent, and $R^7$ and $R^{7'}$ represent an alkyl group),

[Formula 6]

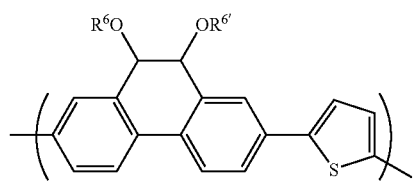

(wherein $R^6$ and $R^{6'}$ represent a silyl group having a substituent),

[Formula 7]

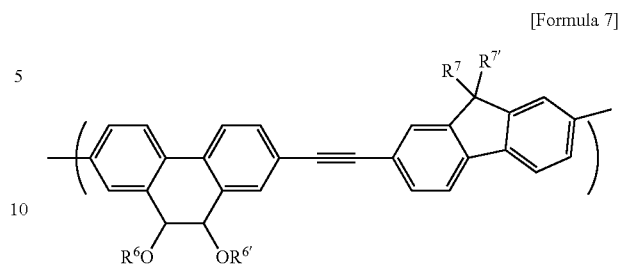

(wherein $R^6$ and $R^{6'}$ represent a silyl group having a substituent, and $R^7$ and $R^{7'}$ represent an alkyl group), and

[Formula 8]

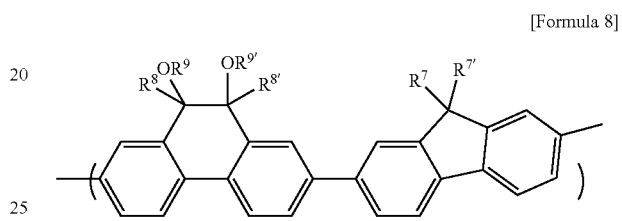

(wherein $R^7$, $R^{7'}$, $R^8$, $R^{8'}$, $R^9$ and $R^{9'}$ represent an alkyl group).

8. The polymer according to claim 4 wherein the alkyl group is an alkyl group having a carbon number of 1-20.

9. A method for producing a polymer compound, in which a polymer compound as claimed in claim 4 is obtained by dehalogenation-polymerizing a dihalide represented by the following formula,

[Formula 1]

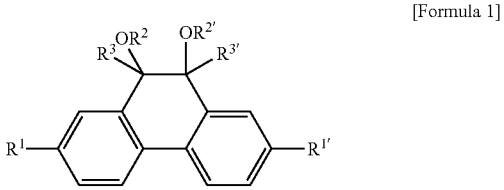

(wherein $R^1$ and $R^{1'}$ represent a halogen, $R^2$ and $R^{2'}$ represent a silyl group having a substituent, and $R^3$ and $R^{3'}$ represent a hydrogen or an alkyl group).

10. The method for producing a polymer compound according to claim 9, wherein the dehalogenation-polymerization is performed in the presence of palladium or nickel compound.

11. A thin film obtained by using polymer compound as claimed in claim 4.

12. The method of claim 9 wherein the silyl group having the substituent is at least one selected from the group consisting of $Si(CH_3)_3, Si(n\text{-}C_4H_9)_3, Si(t\text{-}C_4H_9)_3, Si(CH_3)_2(C_6H_5)$ and $Si(CH_3)_2(n\text{-}C_{18}H_{37})$.

13. The method for producing a polymer compound according to claim 12, wherein the dehalogenation-polymerization is performed in the presence of palladium or nickel compound.

14. The polymer compound of claim 4 wherein the polymer compound is soluble and has heat resistance, electrochemical activity, and fluorescence.

* * * * *